(12) United States Patent
Shibakusa et al.

(10) Patent No.: US 10,390,553 B2
(45) Date of Patent: Aug. 27, 2019

(54) FOOD CONTAINING HISTIDINE AND USE THEREOF

(71) Applicant: AJINOMOTO CO., INC., Tokyo (JP)

(72) Inventors: Tetsuro Shibakusa, Kawasaki (JP); Mayu Sugita, Kawasaki (JP); Ikuko Sasahara, Kawasaki (JP); Naoto Koyama, Kawasaki (JP); Shinobu Seki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/092,809

(22) Filed: Apr. 7, 2016

(65) Prior Publication Data

US 2016/0295904 A1    Oct. 13, 2016

Related U.S. Application Data

(63) Continuation of application No. PCT/JP2014/076990, filed on Oct. 8, 2014.

(30) Foreign Application Priority Data

Oct. 9, 2013 (JP) .................. 2013-212213

(51) Int. Cl.

| | | |
|---|---|---|
| A23L 2/52 | (2006.01) | |
| A61K 9/00 | (2006.01) | |
| A61K 9/08 | (2006.01) | |
| A61K 9/20 | (2006.01) | |
| A61K 9/48 | (2006.01) | |
| A23L 33/175 | (2016.01) | |
| A61K 31/4172 | (2006.01) | |

(52) U.S. Cl.
CPC ............. *A23L 33/175* (2016.08); *A23L 2/52* (2013.01); *A61K 9/0056* (2013.01); *A61K 9/0095* (2013.01); *A61K 9/08* (2013.01); *A61K 9/2013* (2013.01); *A61K 9/4858* (2013.01); *A61K 31/4172* (2013.01); *A23V 2002/00* (2013.01)

(58) Field of Classification Search
CPC ........ A23V 2250/0624; A23V 2002/00; A23V 2200/322; A23V 2200/00; A23L 2/52; A23L 33/175; A61K 31/4172; A61K 31/415; A61K 9/0056; A61K 9/0095; A61K 9/08; A61K 9/2013; A61K 9/4858
See application file for complete search history.

(56) References Cited

U.S. PATENT DOCUMENTS

| | | | | |
|---|---|---|---|---|
| 4,368,204 A | * | 1/1983 | Sato ................ | A23L 33/175 514/400 |
| 5,972,985 A | * | 10/1999 | Thomas ............ | A61K 9/5047 514/400 |
| 6,235,719 B1 | | 5/2001 | Harang | |
| 6,420,342 B1 | * | 7/2002 | Hageman ............ | A61K 31/522 514/23 |
| 2002/0103244 A1 | * | 8/2002 | Matahira ............. | A61K 31/415 514/396 |
| 2006/0159726 A1 | | 7/2006 | Shell et al. | |
| 2006/0292148 A1 | * | 12/2006 | Matsumoto ......... | A61K 31/047 424/145.1 |
| 2007/0065488 A1 | * | 3/2007 | Ishizaki ................ | A61K 35/60 424/439 |
| 2008/0038321 A1 | * | 2/2008 | Tsuji .................... | A61K 31/198 424/439 |
| 2008/0090749 A1 | | 4/2008 | Takahara | |
| 2011/0081392 A1 | | 4/2011 | De Arruda et al. | |

FOREIGN PATENT DOCUMENTS

| | | |
|---|---|---|
| CN | 1993059 A | 7/2007 |
| JP | 9-20661 A | 1/1997 |
| JP | 2006-137706 A | 6/2006 |
| JP | 2008-88162 A | 4/2008 |
| JP | 2008-120754 A | 5/2008 |
| JP | 2011-512392 A | 4/2011 |
| WO | WO 2006/098524 A1 | 9/2006 |
| WO | WO 2009/054360 A1 | 4/2009 |
| WO | WO 2009/103959 A2 | 8/2009 |

OTHER PUBLICATIONS

Takagi et al. (Alimentary Pharmacology & Therapeutics, 2006, p. 1333-1340).*
Ajinomoto (Ajinomoto, 2017).*
Remington's: the Science and Practice of Pharmacy, Nineteenth edition, vol. 1, p. 806, 1995).*
Kuroda et al. (Physiology & Behavior, 92, 2007, 957-962) (Year: 2007).*
Fuke et al. (Physiology & Behavior, 49, 864-868, 1991) (Year: 1991).*
Umeki et al. (J. Clin. Blochem. Nutr. 43, 175-184, 2008) (Year: 2008).*
Sasahara et al.(Physiology & Behavior 147, 2015, 238-244). (Year: 2015).*
Written Opinion dated Jan. 13, 2015 in PCT/JP2014/076990 (submitting English translation only).
Motonaka Kuroda, et al., "Effect of Dried-Bonito Broth on Mental Fatigue and Mental Task Performance in Subjects with a High Fatigue Score" Physiology & Behavior, vol. 92, 2007, pp. 957-962.
S. Kasaoka et al., Nutrition, vol. 20, pp. 991-996 (2004).

* cited by examiner

*Primary Examiner* — Umamaheswari Ramachandran
(74) *Attorney, Agent, or Firm* — Oblon, McClelland, Maier & Neustadt, L.L.P.

(57) ABSTRACT

Ingesting a food etc. which is in a unit package form per meal and contains, in the unit, not less than 0.3 g of histidine as an ingestion amount per meal is effective for improving mental energy and biorhythm.

28 Claims, 13 Drawing Sheets

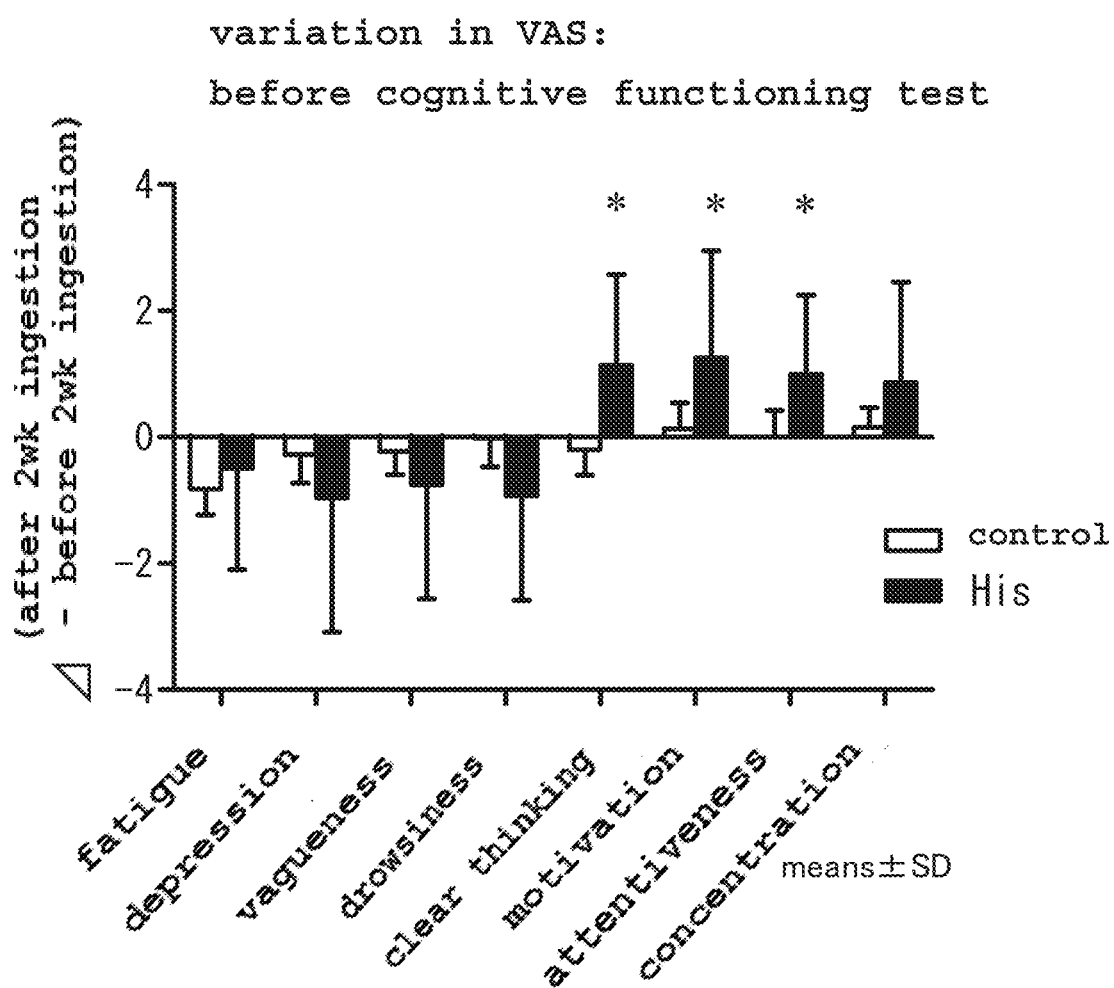

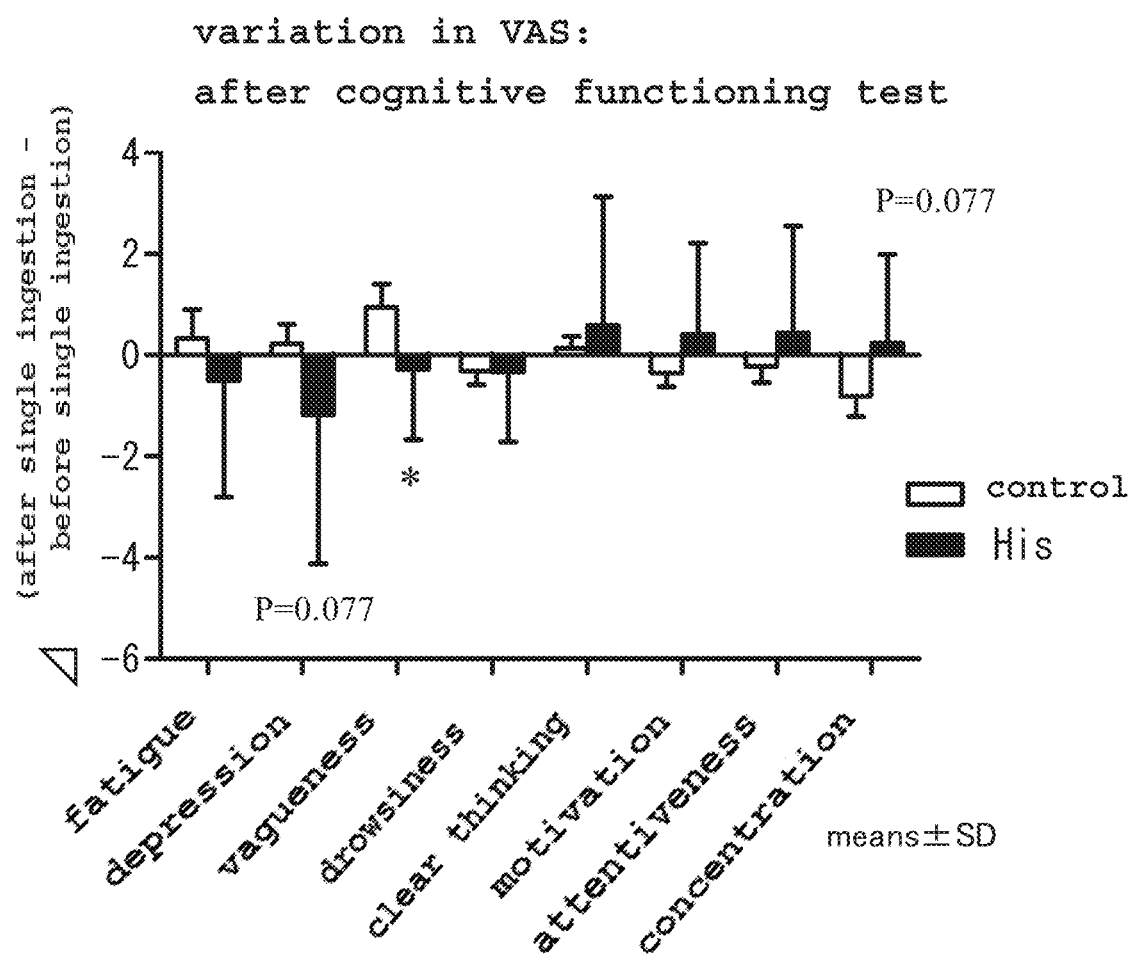

FOOD CONTAINING HISTIDINE AND USE THEREOF

CROSS REFERENCES TO RELATED APPLICATIONS

This application is a continuation of International Patent Application No. PCT/JP2014/076990, filed on Oct. 8, 2014, and claims priority to Japanese Patent Application No. 2013-212213, filed on Oct. 9, 2013, both of which are incorporated herein by reference in their entireties.

BACKGROUND OF THE INVENTION

Field of the Invention

The present invention relates to foods containing histidine and uses thereof.

Discussion of the Background

Histidine is one kind of basic amino acid and is an essential amino acid having an imidazoyl group as a heteroaromatic ring in the side chain. Histidine is an amino acid admitted as a food additive, and contained in many foods. For example, histidine is added as a seasoning or flavor-adjusting agent aiming at firm taste, prevention of diffusion of flavor, and the like, and the content thereof is about 50 mg/100 ml at maximum. In relation to the known function of histidine, an anti-fatigue composition containing histidine or histidine hydrochloride is known (see JP-A-2006-137706, which is incorporated herein by reference in its entirety). This document discloses that the composition improves physical fatigue.

However, there remains a need for histidine-containing foods with improved properties.

SUMMARY OF THE INVENTION

Accordingly, it is one object of the present invention to provide novel foods which contain histidine in a composition and/or form not conventionally present.

It is another object of the present invention to provide novel foods which contain histidine having a new function based on histidine.

It is another object of the present invention to provide novel foods which contain histidine having a less risk of causing side effects.

It is another object of the present invention to provide novel foods which contain histidine and which are capable of effectively improving mental energy.

These and other objects, which will become apparent during the following detailed description, have been achieved by the inventors' discovery that ingestion of not less than a given amount of histidine can express some new functions conventionally not known.

Thus, the present invention provides:

(1) A food in a unit package form per meal, which comprises, in the unit, not less than 0.3 g of histidine as an ingestion amount per meal.

(2) The food of the above-mentioned (1), wherein the content of amino acid other than histidine or a substance convertible to amino acid other than histidine by hydrolysis is not more than 8 g as an ingestion amount per meal based on amino acid other than histidine.

(3) The food of the above-mentioned (1) or (2), further comprising at least one kind of additive selected from excipient, corrigent, and flavor.

(4) The food of the above-mentioned (3), wherein the aforementioned corrigent is citric acid.

(5) The food of any of the above-mentioned (1) to (4), which is in the form of a solid or semi-solid.

(6) The food of any of the above-mentioned (1) to (4), which is in the form of a liquid.

(7) The food of any of the above-mentioned (1) to (4), which is in the form of powder, tablet, granule, or capsule.

(8) The food of any of the above-mentioned (1) to (4), which is in the form of slurry, solution, jelly, or emulsion.

(9) The food of any of the above-mentioned (1) to (4), which is a drink.

(10) The food of any of the above-mentioned (1) to (4), which is confectionery.

(11) The food of any of the above-mentioned (1) to (4), which is jelly, pudding, or yogurt.

(12) The food of any of the above-mentioned (1) to (11), which is a food with health claims.

(13) The food of any of the above-mentioned (1) to (12), which is for improving mental energy.

(13-2) A method of improving mental energy, comprising administering the food of any of the above-mentioned (1) to (12) to a subject in need thereof.

(13-3) The food of any of the above-mentioned (1) to (12), which is for use in the improvement of mental energy.

(14) The food of any of the above-mentioned (1) to (12), which is for improving biorhythm.

(14-2) A method of improving biorhythm, comprising administering the food of any of the above-mentioned (1) to (12) to a subject in need thereof.

(14-3) The food of any of the above-mentioned (1) to (12), which is for use in the improvement of biorhythm.

(15) The food of any of the above-mentioned (1) to (4), which is a drink comprising not less than 1 w/v % of histidine.

(15-2) A drink comprising histidine at not less than 1 w/v %.

(16) The food of any of the above-mentioned (1) to (4), which is a tablet or capsule comprising not less than 0.7 g of histidine.

(16-2) A tablet or capsule comprising not less than 0.7 g of histidine.

(17) A mental energy improving agent in a unit package form per meal, which comprises, in the unit, not less than 0.3 g of histidine as an ingestion amount per meal.

(18) A biorhythm improving agent in a unit package form per meal, which comprises, in the unit, not less than 0.3 g of histidine as an ingestion amount per meal.

(19) The agent of the above-mentioned (17) or (18), wherein the content of amino acid other than histidine or a substance convertible to amino acid other than histidine by hydrolysis is not more than 8 g as an ingestion amount per meal based on amino acid other than histidine.

(20) The agent of any of the above-mentioned (17) to (19), further comprising at least one kind of additive selected from excipient, corrigent and flavor.

(21) The agent of the above-mentioned (20), wherein the aforementioned corrigent is citric acid.

(22) The agent of any of the above-mentioned (17) to (21), which is in the form of a solid or semi-solid.

(23) The agent of any of the above-mentioned (17) to (21), which is in the form of a liquid.

(24) The agent of any of the above-mentioned (17) to (21), which is in the form of powder, tablet, granule or capsule.

(25) The agent of any of the above-mentioned (17) to (21), which is in the form of slurry, solution, jelly or emulsion.

(26) A container-packed drink, comprising histidine at not less than 0.3 g as an ingestion amount per meal.

(27) The drink of the above-mentioned (26), which is for improving mental energy.

(27-2) A method of improving mental energy, comprising administering the drink of the above-mentioned (26) to a subject in need thereof.

(27-3) The drink of the above-mentioned (26), which is for use in the improvement of mental energy.

(28) The drink of the above-mentioned (26), which is for improving biorhythm.

(28-2) A method of improving biorhythm, comprising administering the drink of the above-mentioned (26) to a subject in need thereof.

(28-3) The drink of the above-mentioned (26), which is for use in the improvement of biorhythm.

Effect of the Invention

Ingestion of the food etc. containing histidine of the present invention for a long term or single ingestion thereof can effectively improve mental energy. Since the food etc. containing histidine of the present invention contain amino acid as an active ingredient, they have less fear of causing side effects and are superior in safety, and can also be consecutively used everyday.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 4C shows variation of each index in VAS before cognitive functioning test. *: paired t-test, $p<0.05$.

FIG. 5C shows variation of each index in VAS after cognitive functioning test. *: paired t-test, $p<0.05$.

DETAILED DESCRIPTION OF THE PREFERRED EMBODIMENTS

Figure 1A:
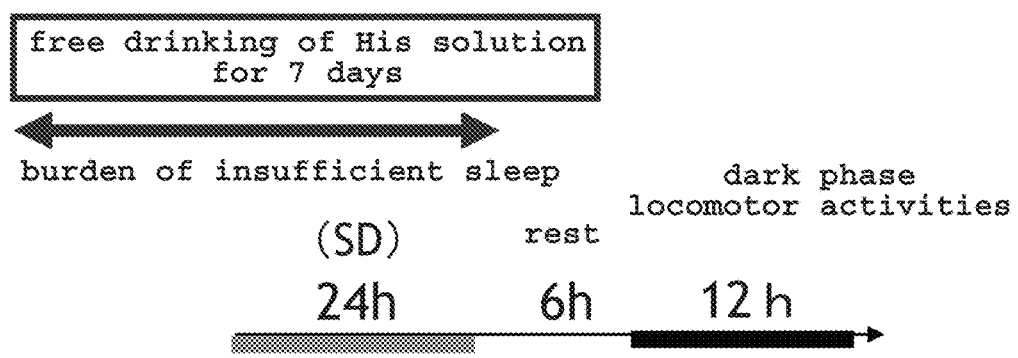
FIG. 1A shows the protocol for verifying variation, by continuous histidine administration, in locomotor activities (indices of mental energy, particularly motivation) in the dark phase of mouse after burden of insufficient sleep.

The mode of embodiment of the present invention is explained below.

The essence of the present invention includes novel uses of histidine, foods suitable for such uses, and the like. Histidine is an essential amino acid having the structural formula: $HOOCCH(NH_2)CH_2$-5-imidazol. The "substance convertible to histidine by hydrolysis" is a substance that affords histidine by hydrolysis (particularly in vivo hydrolysis), and typical examples thereof include proteins and peptides containing histidine as a constituent unit. A substance that affords histidine by hydrolysis produces histidine by hydrolysis in the body after ingestion, and is expected to provide an effect similar to that obtained when histidine is ingested from the start.

The histidine to be used in the present invention may be one extracted and purified from naturally-present animals, plants and the like, or one obtained by a chemical synthesis method, a fermentation method, an enzyme method or a gene recombination method. Any of L-form, D-form, and DL-form can be used.

The histidine used in the present invention may be in the form of a salt. The form of the salt may be, for example, an acid addition salt, a salt with a base, and the like, and pharmacologically acceptable salts are preferable. Examples of such salts include salts with inorganic acids, salts with organic acids, salts with inorganic bases, and salts with organic bases.

Examples of the salt with an inorganic acid include salts with a hydrohalic acid (hydrochloric acid, hydrobromic acid, hydroiodic acid, etc.), sulfuric acid, nitric acid, phosphoric acid, and the like.

Examples of the salt with an organic acid include salts with formic acid, acetic acid, propionic acid, oxalic acid, succinic acid, maleic acid, fumaric acid, citric acid, and the like.

Examples of the salt with an inorganic base include salts with alkali metals such as sodium, potassium, lithium, and the like, salts with alkaline earth metals such as calcium, magnesium and the like, salt with ammonium, and the like.

Examples of the salt with an organic base include salts with ethylenediamine, propylenediamine, ethanolamine, monoalkylethanolamine, dialkylethanolamine, diethanolamine, triethanolamine, and the like.

The food etc. in a unit package form per meal in the present invention contains not less than 0.3 g of histidine or a substance convertible to histidine by hydrolysis (amount based on histidine) per meal (i.e., ingestion amount per meal). Since such foods etc. permit easy ingestion of a large amount of histidine, they easily enjoy the effects by the novel action mentioned below. In the present specification, the food etc. is a concept widely encompassing oral ingestible matters, and includes not only what is called "food" but also a drink, health aid food, food with health claims, supplement, and the like. Examples of the unit package form per meal include a form that defines a given amount in a pack, package, bottle, etc. in the case of drink, candy, chewing gum, jelly, pudding, yogurt and the like, and package and the like can define a given amount in the case of granular, powdery and slurry foods. Alternatively, a form such as a container and the like indicating the ingestion amount per meal can be mentioned. In the present specification, the food etc. includes an agent which is ingested for a particular purpose, different from those daily ingested to retain nutrition of the body, and therefore, the "food etc." of the present invention means the same as the "food and agent" of the present invention.

The food and agent in "a unit package form per meal" are foods and agents in the form for which the amount to be ingested per meal has been determined in advance.

Being "based on histidine" in the content of histidine or a substance convertible to histidine by hydrolysis in a food etc. means when histidine per se is contained, the weight of histidine is taken note of and, when a substance convertible to histidine by hydrolysis is contained, the weight of histidine when all the substances convertible to histidine are converted to histidine is taken note of. When a food etc. contains both histidine and a substance convertible to histidine by hydrolysis, the content of histidine in the food etc. is the total weight of the weight of histidine obtained by converting, by hydrolysis, all substances convertible to histidine by hydrolysis, and histidine presented from the start.

The content of histidine or a substance convertible to histidine by hydrolysis per meal is not less than 0.3 g, preferably not less than 0.7 g, more preferably not less than 1 g, further preferably not less than 1.2 g, further preferably not less than 1.6 g, based on histidine, from the aspects of easy addition to the food etc. and the effect afforded by the presence thereof. From the aspects of eating experiences obtained from known findings (Food Safety Commission of Japan, Feed/Fertilizer, etc. Expert Committee, April 2010, exempted evaluation report histidine, safety and effectiveness information of "health food" (National Institute of Health and Nutrition HP https://hfnet.nih.go.jp/)) and easiness of packaging and ingestion, the above-mentioned content is preferably not more than 23 g, more preferably not more than 20 g, further preferably not more than 10 g, particularly preferably not more than 4 g.

When the content of amino acids other than histidine in the above-mentioned food etc. is high, the effect of histidine mentioned below may not be sufficiently exhibited. Therefore, the content of amino acids other than histidine or a substance convertible to an amino acid other than histidine by hydrolysis is, based on amino acid other than histidine, generally not more than 8 g, not more than 6 g, not more than 4 g, preferably not more than 2 g, per meal (i.e., ingestion amount per meal). More preferably, it is not more than 50 mg, and substantial absence thereof is preferable.

The "amino acid" is a generic term for an organic compound having both an amino group ($-NH_2$) and a carboxyl group ($-COOH$). Therefore, the amino acid other than histidine in the present invention is an organic compound other than histidine, which has both an amino group and a carboxyl group. The "substance convertible to amino acid other than histidine by hydrolysis" is a substance that affords an organic compound having both an amino group and a carboxyl group (excluding histidine) by hydrolysis (particularly in vivo hydrolysis), and typical examples thereof include proteins and peptides containing an amino acid other than histidine as a constituent unit.

Being "based on amino acid other than histidine" in the content of amino acid other than histidine or a substance convertible to histidine by hydrolysis in a food etc. means that the total of the weight of amino acid other than histidine and the weight of amino acid other than histidine when a substance convertible to amino acid other than histidine by hydrolysis is converted to amino acid other than histidine by hydrolysis is taken note of.

The form of histidine or a substance convertible to histidine by hydrolysis to be contained in the food etc. is not particularly limited, and may be a powder or granule, slurry, tablet confectionery, capsule, solution, jelly, or emulsion. Of these, granules and powders are preferable, in view of easy portability and easy packaging. In addition, a solution, jelly and slurry are also preferable in view of easy ingestion.

For example, when the food etc. are what is called health foods, a form wherein not less than 0.3 g of granular histidine is packed in a unit of ingestion per meal and the like can be mentioned; when the food etc. are nutritional drinks, a form wherein the above-mentioned amount is suspended or dissolved to give a drink, which is packed in a bottle etc. for a single consumption and the like can be mentioned.

The form of the food etc. of the present invention is not particularly limited, and may be solid or semi-solid, or liquid such as a powder, tablet, granule, slurry, capsule, solution, jelly, emulsion, and the like. In view of easy portability and easy packaging, a powder, tablet, and granule are preferable. From the aspect of easy ingestion, a slurry is also preferable.

The food etc. of the present invention is also preferably produced as drink, confectionery, jelly, pudding, or yogurt, from the aspect of easy ingestion. The drink includes not only those served as a solution, a suspension, and the like in bottle, can, paper pack, and the like, but also those served for drinking after extraction and dissolution such as tea, coffee, powder drinks, and the like. As used herein, confectionery refers to favorite foods such as sweet stuffs and the like, which are eaten other than meals, and examples thereof include a candy, chewing gum, tablet confectionery, and the like.

In the case of drinks, histidine at a concentration of not less than 1 w/v % can be ingested in necessary quantities for necessary times. The concentration is preferably not less than 3 w/v %, more preferably not less than 5 w/v %. The concentration is generally not more than 30 w/v %, preferably not more than 20 w/v %, more preferably not more than 17 w/v %, further preferably not more than 10 w/v %.

In the case of tablet or capsule form, it can be ingested in necessary quantities for necessary times when not less than 100 mg (i.e., not less than 0.1 g) of histidine is contained. The content is preferably not less than 250 mg (i.e., not less than 0.25 g), more preferably not less than 300 mg (i.e., not less than 0.3 g), further preferably not less than 700 mg (i.e., not less than 0.7 g). In the case of tablet, when histidine is contained at not less than 65 weight %, a tablet having an easily ingestible size can be obtained. The content is preferably not less than 70 weight %, more preferably not less than 80 weight %. The content is generally not more than 95 weight %, preferably not more than 90 weight %.

Examples of the application target of the food etc. of the present invention include experiment animals such as rodents (e.g., a mouse, rat, hamster, guinea pig, and the like), rabbit and the like, pets such as a dog, cat, and the like, domestic animals and poultry such as bovine, swine, goat, horse, sheep, chicken, and the like, primates such as a monkey, orangutan, chimpanzee, and the like, human, and the like, and human is particularly preferable. For application to an animal other than human, the dose of the food etc. of the present invention can be appropriately moderated based on the general description of the dose for human, which is described in the present specification, and further considering the body weight or size of the animal, or the condition, sensitivity and the like of the administration subject at the time of administration.

One embodiment of the food etc. of the present invention is a container-packed drink comprising histidine, and particularly, a container-packed drink containing not less than 0.3 g (preferably, not less than 0.7 g, more preferably not less than 1 g, further preferably not less than 1.2 g, particularly preferably not less than 1.6 g) of histidine as an ingestion amount per meal is provided.

As for the content of histidine in the container-packed drink of the present invention, the ingestion amount per meal of histidine is preferably not more than 23 g from the aspects of eating experiences obtained from known finding (mentioned above) and easiness of packaging and ingestion.

The "drink" in the container-packed drink of the present invention includes, for example, the food etc. of the present invention provided as a drink, specifically, drinks such as tea drinks (e.g., green tea, oolong tea, black tea, etc.), alcohol drinks (e.g., beer, wine, sake, distilled spirits, ume (Japanese plum) wine, low-malt beer, whiskey, brandy, etc.), beverage (e.g., sports drinks, isotonic drinks, mineral water, coffee drinks, etc.), juice (e.g., fruit juice, vegetable juice, etc.) and the like, liquid seasoning (e.g., soy sauce, vinegar, liquor, sweet sake for seasoning, soup stock, etc.), liquid supplement (e.g., nutritional supplement drink, beauty drink, energy drink, etc.), and the like. A container-packed drink can be produced by injecting or filling the drink in a desired container. The drink may be those served as a solution, a suspension, and the like, and also may be those served for drinking after extraction and dissolution such as tea leaves, coffee beans, powder drinks, and the like.

A container to be used for the container-packed drink of the present invention is appropriately selected according to the object. Generally, a can, bottle, PET bottle, paper container, aluminum pouch, and the like can be mentioned. The volume is not particularly limited, and one or more units may be directly housed in one container wherein ingestion amount per meal is one unit, or concentrated drink may be filled in a container.

The container-packed drink of the present invention may be in a unit package form per meal. Examples of the form include a container defining a given amount, a container indicating the ingestion amount per meal, and the like.

The container-packed drink of the present invention is one embodiment of the food etc. of the present invention, and therefore, it is needless to say that the "food etc. of the present invention" described in the present specification encompasses "the container-packed drink of the present invention".

The invention relating to the novel use of histidine is now explained. The novel use in the present invention is a use as a food for improving mental energy (mental energy improving agent), or a food for improving biorhythm (biorhythm improving agent). The agent in the present invention is understood to mean one ingested for a particular purpose, different from those that are daily ingested by human to retain nutrition of the body for survival.

Food and Agent for Improving Mental Energy.

In one embodiment, the present invention provides a food etc. for improving mental energy, which is in a unit package form per meal, and contains not less than 0.3 g of histidine as an ingestion amount per meal in the unit.

In the present specification, "mental energy" is a concept scientifically defined, in a series of workshop held by the International Life Sciences Institute (ILSI) North American branch, as "the ability to perform mental tasks, the intensity of feelings about energy/fatigue, and the motivation to accomplish mental and physical tasks" (reference document: Do specific dietary constituents and supplements affect mental energy? Review of the evidence Nutrition Reviews 2010 Vol. 68(12):697-718, which is incorporated herein by reference in its entirety). Mental energy is a three-dimensional constituent concept constituted of (1) mood (transient feelings about fatigue or energy), (2) motivation (determination and enthusiasm), and (3) cognition (sustained attention, awakening, memory, learning, speed of information processing, etc.). Generally, it is considered that all 3 factors mentioned above do not need to be changed to influence the mental energy.

Examples of the factors that influences mental energy include genetic factors, nutrition, pain, sleep, and the like (reference document: Mental Energy: Developing a Model for Examining nutrition related claims Nutrition Reviews, Vol. 64, No. 7 Jul. 2006: (II)S2-6, which is incorporated herein by reference in its entirety). As a method of increasing mental energy, ingestion of food, food component and/or supplement, motility, sufficient sleep, and short nap and the like are recited. As a factor that decreases mental energy, sleep-related distress (sleep loss, sleep disorder, sleep insufficiency, etc.) and fatigue are considered (reference document: Rhythms of mental performance (2008) Mind, Brain, and Education, 2 (1), pp. 7-16, which is incorporated herein by reference in its entirety).

The food etc. of the present invention can be applied to improve mental energy. In the present specification, "improve" is used to indicate a meaning encompassing promotion, enhancement, betterment, and maintenance of mental energy.

The food etc. of the present invention is particularly preferably applied to improve mental energy during sleep insufficiency, which is a representative factor that decreases mental energy. Here, the sleep insufficiency can be judged according to a method known per se and, for example, the Pittsburgh Sleep Quality Index (PSQI) that evaluates subjective sleep quality, polysomnography that measures plural indices including brain wave measurement and the like can be used. Preferably, PSQI is used, and a value of not less than 6 can be evaluated as sleep insufficiency.

The mental energy can be evaluated by a method known per se as an evaluation method of mood, motivation, cognition. Examples of such methods include subjective evaluation methods such as visual analog scale (VAS), Profile of Mood States (POMS), and the like, and objective evaluation methods such as CogHealth (Coghealth: manufactured by Cogstate Ltd., Health Solution, Inc. provide) capable of measuring a brain function which will be declined due to fatigue and aging.

In the present specification, "mood" is a concept including transient feeling about fatigue and transient feeling about energy, and is evaluated based on the POMS, and scores of depression, vagueness, clear thinking, concentration, and attentiveness in VAS.

In the present specification, "motivation" is a concept including determination and enthusiasm, and is evaluated based on the scores of motivation in VAS and the level of decrease in locomotor activities due to sleep disorder.

In the present specification, "cognition" is a concept including sustained attention, awakening, memory, learning, speed of information processing, and is evaluated based on the reaction rate in the delayed recall task in a cognitive functioning test (CogHealth), scores of attentiveness and clear thinking (awakening) in VAS, and the level of decrease in working memory due to sleep disorder.

When VAS is utilized, for example, scores are measured before and after continuous ingestion for a given period or single ingestion of a test sample, and when the score of clear thinking, motivation, concentration or attentiveness significantly increases or the score of depression or vagueness significantly decreases after test sample ingestion, the mental energy, particularly "mood", can be evaluated to have been improved. Particularly, one or more indices selected from the group consisting of attentiveness, concentration, depression and vagueness in VAS can be significantly improved by ingesting the food etc. of the present invention.

When, for example, scores of motivation in VAS are measured before and after continuous ingestion for a given period or single ingestion of a test sample, and the scores significantly increase after test sample ingestion, the mental energy, particularly "motivation" can be evaluated to have been improved. Particularly, the index of motivation in VAS can be significantly improved by ingesting the food etc. of the present invention.

For example, when scores of attentiveness or clear thinking (awakening) in VAS are measured before and after continuous ingestion for a given period or single ingestion of a test sample, and the scores significantly increase after test sample ingestion, mental energy, particularly "cognition" can be evaluated to have been improved. The index of attentiveness or clear thinking (awakening) in VAS can be significantly improved by ingesting the food etc. of the present invention.

When POMS is utilized, for example, scores are measured before and after continuous ingestion for a given period or single ingestion of a test sample, and when the score of vigor significantly increases or the score of tension-anxiety, depression, anger, fatigue, or confusion significantly decreases after test sample ingestion, mental energy, particularly "mood", can be evaluated to have been improved. In addition, for example, when the T score of fatigue factor (F factor) is not less than 60 by subjective evaluation by POMS, mental energy can be evaluated to have decreased. Particularly, an index of fatigue can be significantly improved by ingesting the food etc. of the present invention.

When CogHealth is utilized, for example, mental energy can be judged by evaluating the accuracy rate or reaction time in each task of simple reaction (awakening), selective reaction (awakening), working memory (memory), delayed recall (memory), and distraction of attention (sustained attentiveness). Particularly, the state of "cognition" can be judged by evaluating the reaction time in delayed recall task. For example, when a test is performed after continuous ingestion of a test sample or control sample for a given period, and the reaction time, particularly the reaction time in delayed recall task, significantly decreases in a test sample ingestion group as compared to control sample ingestion group, the mental energy, particularly "cognition" can be evaluated to have been improved by ingesting the test sample. Particularly, the reaction time in the delayed recall task can be significantly lowered by ingesting the food etc. of the present invention.

When locomotor activities due to sleep disorder are measured in the evaluation of "motivation", changes in the locomotor activities of a target with sleep insufficiency only need to be measured by a method known per se. For example, a data acquisition analysis system containing an infrared sensor (e.g., NS-DAS-32 (NeuroScience, Inc) and the like) can be utilized. For example, measurement is performed after continuous ingestion of a test sample or a control sample for a given period by a target with sleep insufficiency and, when a decrease in the locomotor activities is suppressed in a test sample ingestion group as compared to a control sample ingestion group, the ingestion of the test sample can be evaluated to have improved mental energy, particularly "motivation". A decrease in the locomotor activities due to sleep disorder can be suppressed by ingesting the food etc. of the present invention.

When working memory due to sleep disorder is measured in the evaluation of "cognition", working memory of a target with sleep insufficiency only needs to be measured by a method known per se. For example, in a target other than human, alternation behavior in the Y-maze test described in the below-mentioned Examples is measured, and a decrease in the alternation behavior can be evaluated as a decrease in the working memory. Measurement is performed after continuous ingestion of a test sample or a control sample for a given period by a target with sleep insufficiency and, when a decrease in the working memory is suppressed in a test sample ingestion group as compared to a control sample ingestion group, the mental energy, particularly "cognition" can be evaluated to have been improved by the ingestion of the test sample. A decrease in the working memory due to sleep disorder can be suppressed by ingesting the food etc. of the present invention.

The food etc. of the present invention as a food etc. for improving mental energy is a food etc. containing histidine or a substance convertible to histidine by hydrolysis. The ingestion amount of the aforementioned food etc. for this use varies depending on the age, body weight, symptom of the target, administration method and the like. For a male human adult, it is generally 0.3 to 23 g/day, preferably 0.7 to 8 g/day, more preferably 0.7 to 4 g/day, based on histidine. Being "based on histidine" means as mentioned above. When histidine forms a salt, the ingestion amount is calculated after converting a salt thereof to a free form. A value not less than the lower limit in the aforementioned numerical value is sufficient to afford the aforementioned effect. However, when the ingestion amount is high, the ingestion becomes difficult, or the cost tends to be high. The food etc. in the form of an ingestion amount unit per meal is also useful for facilitating the management of the ingestion amount of histidine.

Since the food etc. of the present invention has high safety, it may be prophylactically ingested before emergence of a symptom of decrease in the mental energy. In addition, since the food etc. of the present invention affords a mental energy improving effect in a short time (e.g., about 1 hr) by a single ingestion, they may be therapeutically ingested after emergence of a symptom of decrease in the mental energy. When the food etc. of the present invention is ingested not less than two times, the ingestion period thereof is not particularly limited as long as the effect of the present invention is obtained, and is generally not less than one day (e.g., 7 days, 14 days, etc.).

Food and Agent for Improving Biorhythm.

In one embodiment, the present invention provides a food etc. for improving biorhythm in a unit package form per meal, which contains, in the unit, not less than 0.3 g of histidine as an ingestion amount per meal.

In the present specification, "biorhythm" refers to the rhythm of life phenomena inherently present in organisms, particularly circadian rhythm. Biorhythm can be investigated by examining the behavior start time of one day by behavior observation of the individual or measuring the oscillation of expression of a known clock gene (e.g., Bmal1, Dbp, Per1, Per2, Reverb-alpha, etc.) by a conventional method (reference document: The Journal of Clinical Investigation 2010 July; 120(7):2600-9, which is incorporated herein by reference in its entirety).

The term "improvement of biorhythm" means that the abnormality of biorhythm is improved. More particularly, it means that various symptoms due to asynchrony of biorhythm with the outside world, for example, jet lag-like symptoms including early wakening, headache, tinnitus, palpitation, nausea, abdominal pain and diarrhea, fatigue-like symptoms including a decrease in clear thinking, motivation, attentiveness and concentration, depression, daytime drowsiness, languor and the like are improved. Furthermore, improvement of biorhythm includes normalization of diurnal rhythm, improvement of circadian rhythm sleep disorder, improvement of delayed sleep phase syndrome, improvement of jet lag, improvement of seasonal depression, and improvement of age-related circadian rhythm modulation, and also includes promoted formation of biorhythm in young people.

Ingestion of the food etc. of the present invention can, for example, advance circadian rhythm, and shorten the length of the cycle. Since abnormality of biorhythm is often caused by regression of circadian rhythm, the food etc. of the present invention is useful for the normalization of biorhythm (e.g., bringing circadian rhythm close to 24 hr in human). Therefore, the food etc. of the present invention can be utilized as, for example, a diurnal rhythm normalizing agent, a biorhythm improving agent, a circadian rhythm sleep disorder improving agent, a delayed sleep phase syndrome improving agent, a therapeutic agent for jet lag, a prophylactic agent for jet lag, or an agent for improving ill health associated with working in shifts.

It is known that the phase of oscillation of expression of a clock gene responsible for circadian rhythm advances in mammal along with aging. However, ingestion of the food etc. of the present invention can suppress such phase shift. Therefore, the food etc. of the present invention can be utilized as an agent for improving various symptoms due to asynchrony of biorhythm with the outside world, particularly age-related circadian rhythm modulation.

The ingestion amount of the aforementioned food etc. for use for the improvement of biorhythm is the same as the ingestion amount of a food etc. for improving mental energy.

Since the food etc. of the present invention has high safety, they may be prophylactically ingested before emergence of abnormality of biorhythm. In addition, the food etc. of the present invention may be therapeutically ingested after emergence of abnormality of biorhythm. The ingestion period of the food etc. of the present invention is not particularly limited as long as the effect of the present invention is obtained, and is generally not less than one day (e.g., 4 days, 7 days, 9 days, 14 days, etc.).

The food etc. of the present invention can contain various additives in an attempt to provide same in a form easier to take. Specifically, corrigent, flavor, excipient, lubricant, and the like can be mentioned, and any additive can be utilized as long as addition to food etc. is admitted. Examples of the corrigent include souring agents such as ascorbic acid, tartaric acid, citric acid, malic acid, and salts of these, and the like, sweeteners such as aspartame, stevia, sucralose, glycyrrhizinic acid, thaumatin, acesulfame potassium, saccharin, saccharin sodium, and the like, and the like. As corrigent, citric acid is preferably used. Examples of the flavor include synthetic flavor compounds such as L-menthol and the like, citrus essential oils such as orange, lemon, lime, grapefruit and the like, plant essential oils such as flower essential oil, peppermint oil, spearmint oil, spice oil and the like, and the like. Examples of the excipient include lactose, sucrose, D-mannitol, starch, cornstarch, crystalline cellulose, light anhydrous silicic acid, and the like. Examples of the lubricant include magnesium stearate, calcium stearate, talc, colloidal silica, and the like.

Commercial Package.

The food etc. of the present invention can also be formed as a commercial package also containing a written matter describing explanation items relating to use, efficacy, eating/drinking method, and the like.

Other features of the invention will become apparent in the course of the following descriptions of exemplary embodiments which are given for illustration of the invention and are not intended to be limiting thereof.

EXAMPLES

Example 1: Verification of Change of Locomotor Activities in the Dark Phase (Index of Mental Energy, Particularly Motivation) after Burden of Insufficient Sleep and Effect of Continuous Administration of Histidine (His)

Using CD2F1 mice (9-week-old) and as shown in the experiment protocol of FIG. 1A, the mice were chronically allowed to drink a 1.2 w/v % L-histidine solution for 7 days in the histidine ingestion group (SD+His) to achieve a dose of 1.2 g/kg body weight/day. Water was given to the control group (CON) and the solvent ingestion group (SD+solvent). Then, the sleep disorder group (SD) was burdened by insufficient sleep for one day by filling water in the breeding cage at the depth of 0.5 cm. The burden was released at 6 hr from the start of the light phase (ZT6), and the mice were placed back in the home cage and allowed to rest for 6 hr. The control group was reared without burden in the home cage. Thereafter, they were transferred into a cage set under a locomotor activity measurement infrared sensor (Digital acquisition system; NS-DAS-32, Neuroscience Inc, Tokyo, Japan) under fasting and water-deprivation. The locomotor activities were measured and the data was collected by a multidigital counter (Neuroscience Inc, Tokyo, Japan).

Figure 1B:
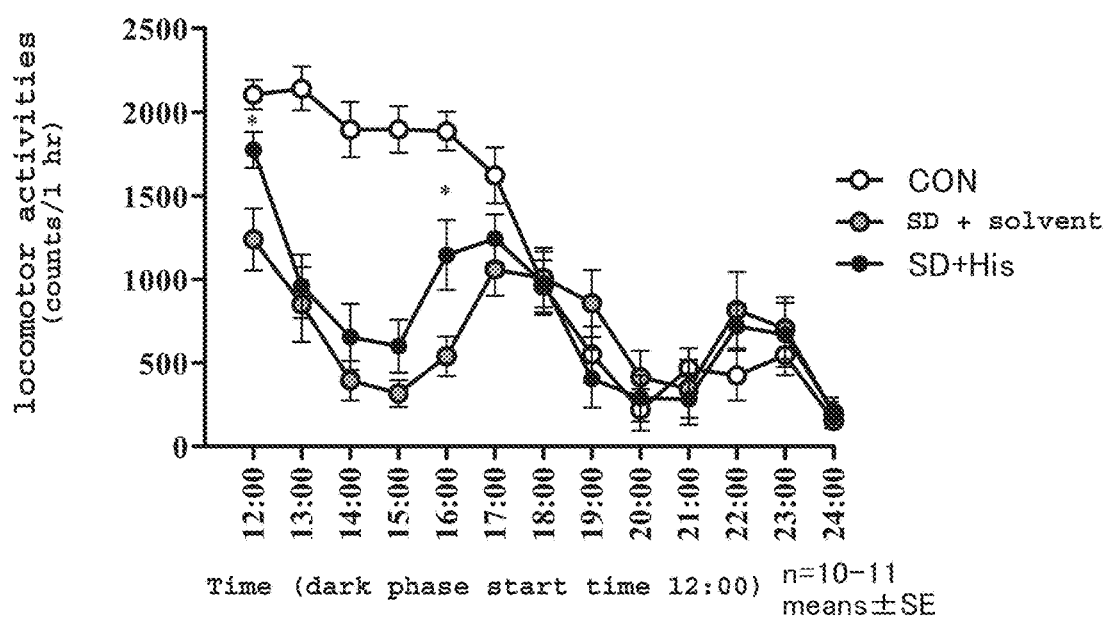
FIG. 1B shows the measurement results of locomotor activities in the dark phase. *: Dunnett's test after one-way analysis of variance, $p<0.05$.
Figure 1C:
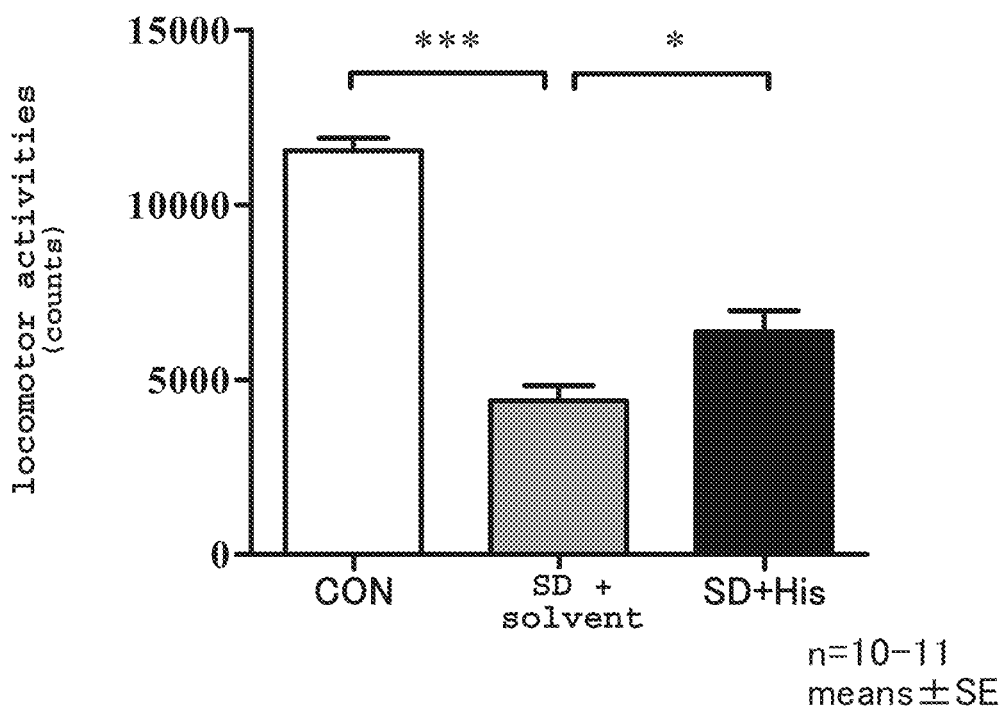
FIG. 1C shows cumulative locomotor activities for the former half (6 hr) of the dark phase. ***: Dunnett's test after one-way analysis of variance, $p<0.001$, *: Dunnett's test after one-way analysis of variance, $p<0.05$.

The results are shown in FIGS. 1B and C. The burden of insufficient sleep decreased the locomotor activities in the dark phase. The group allowed to freely ingest the histidine solution for 7 days (SD+His) showed a significant suppression of a decrease of locomotor activities in the dark phase as compared to the solvent ingestion group (SD+solvent).

From the above results, it was clarified that an agent containing histidine improves mental energy, particularly motivation.

Example 2: Verification of Change of Locomotor Activities Under Novel Environment (Index of Mental Energy, Particularly Motivation) after Burden of Insufficient Sleep and Effect of Single Administration of Histidine (His)

Figure 2A:
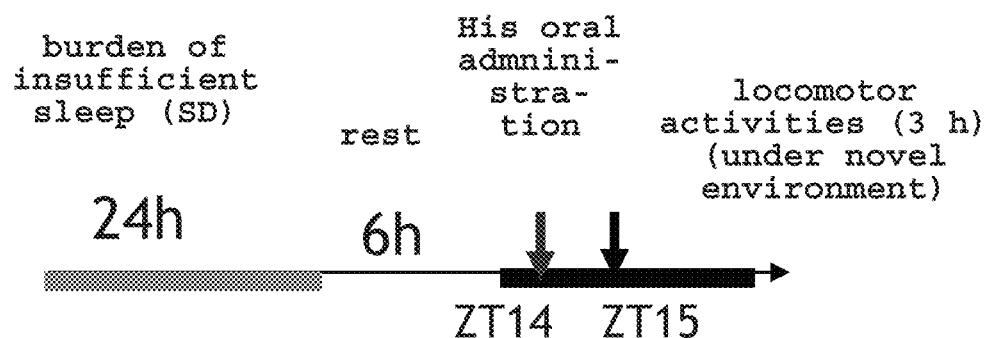
FIG. 2A shows the protocol for verifying variation, by single administration of histidine, in locomotor activities (indices of mental energy, particularly motivation) under novel environment of mouse after burden of insufficient sleep.

Using CD2F1 mice (9-10-week-old) and as shown in the experiment protocol of FIG. 2A, a burden of insufficient sleep is applied to sleep disorder group (SD) for one day. The burden was released at ZT6, and the mice were placed back in the home cage and allowed to rest for 6 hr. The control group (CON) was reared without burden in the home cage. A 1.2 w/v % L-histidine solution was orally administered to a histidine administration group (SD+His) at 2 hr after the start of the dark phase after burden of insufficient sleep (ZT14), to achieve an L-histidine dose of 1.2 g/kg body weight. A solvent (water) was orally administered to the solvent administration group (SD+solvent) and the control group (CON). The locomotor activities under novel environment were measured for 3 hr from 3 hr after the start of the dark phase (ZT15).

Figure 2B:
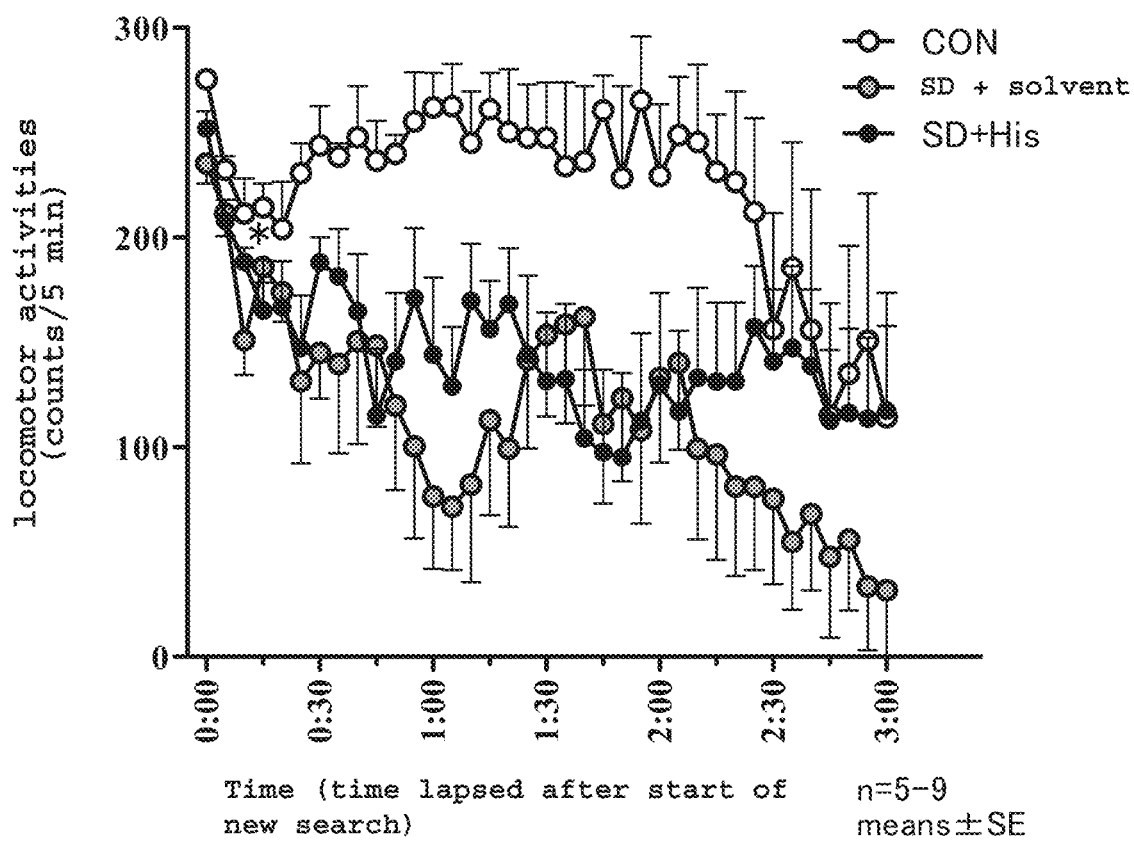
FIG. 2B shows the measurement results of locomotor activities under novel environment. *: Dunnett's test after one-way analysis of variance, $p<0.05$.

The results are shown in FIG. 2B. The burden of insufficient sleep decreased the locomotor activities. However, the group orally administered with the histidine solution (SD+His) showed a tendency of suppression of a decrease in the locomotor activities as compared to the solvent administration group (SD+solvent).

From the above results, it was clarified that an agent containing histidine improves mental energy, particularly motivation.

Example 3: Verification of Change of Short-Working Memory (Index of Mental Energy, Particularly Cognition) after Burden of Insufficient Sleep and Effect of Single Administration of Histidine (His)

Figure 3A:
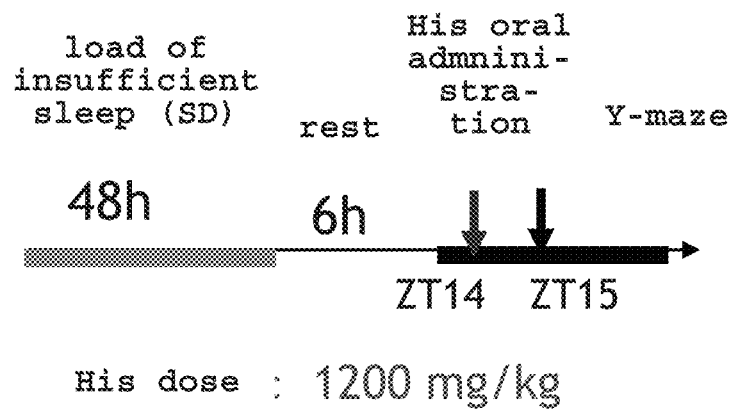
FIG. 3A shows the protocol for verifying variation, by single administration of histidine, in short-working memory (indices of mental energy, particularly cognition) of mouse after burden of insufficient sleep.

Using CD2F1 mice (9-week-old) and as shown in the experiment protocol of FIG. 3A, a burden of insufficient sleep is applied to sleep disorder group (SD) for two days. The burden was released at ZT6, and the mice were placed back in the home cage and allowed to rest for 6 hr. The control group (CON) was reared without burden in the home cage. A L-histidine solution was orally administered to a histidine administration group (SD+His) at 2 hr after the start of the dark phase after burden of insufficient sleep (ZT14), to achieve an L-histidine dose of 1.2 g/kg body weight. A solvent (water) was orally administered to the solvent administration group (SD+solvent) and the control group (CON). The Y-maze test was performed at 3 hr from the start of the dark phase (ZT15), and short-working memory was measured.

Figure 3B:
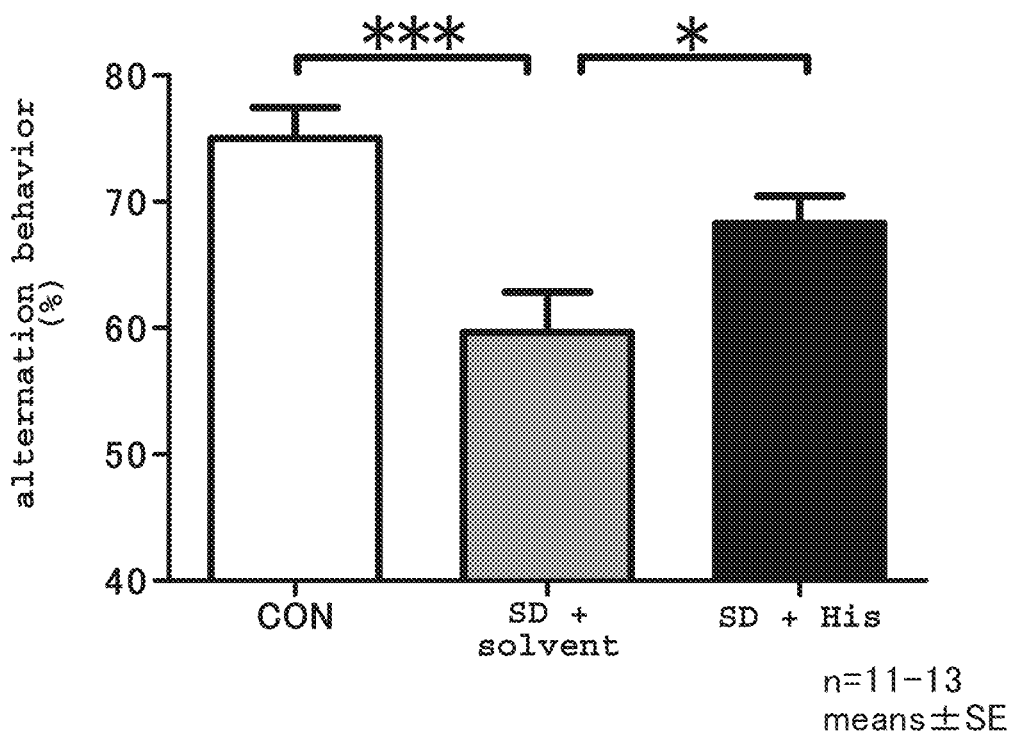
FIG. 3B shows the measurement results of alternation behavior. ***: Dunnett's test after one-way analysis of variance, $p<0.001$, *: Dunnett's test after one-way analysis of variance, $p<0.05$.

The results are shown in FIG. 3B. The burden of insufficient sleep decreased the alternation behavior. However, the group orally administered with the histidine solution (SD+His) showed a significant suppression of a decrease of alternation behavior as compared to the solvent administration group (SD+solvent). That is, single administration of histidine suppressed a decrease in the short-working memory after burden of insufficient sleep.

From the above results, it was clarified that an agent containing histidine improves mental energy, particularly cognition.

Example 4: Verification of Effect of Histidine (His) Ingestion for 14 Days in Males Feeling Decrease in the Sleep Quality and Fatigue Twenty males of 45 years old to less than 65 years old, who received total evaluation of not less than 17 points in the "self-diagnosis fatigue questionnaire" (Fatigue Science Laboratory Inc.) performed in advance, felt decrease in the quality of sleep (generally PSQI≥6), and obtained fatigue factor T scores of not less than 60 points in POMS, were selected, and randomly divided into 2 groups (10 per group). A crossover test, including ingesting histidine and control food (equal volume of cellulose) each for 14 days, was performed in each group.

Figure 4A:
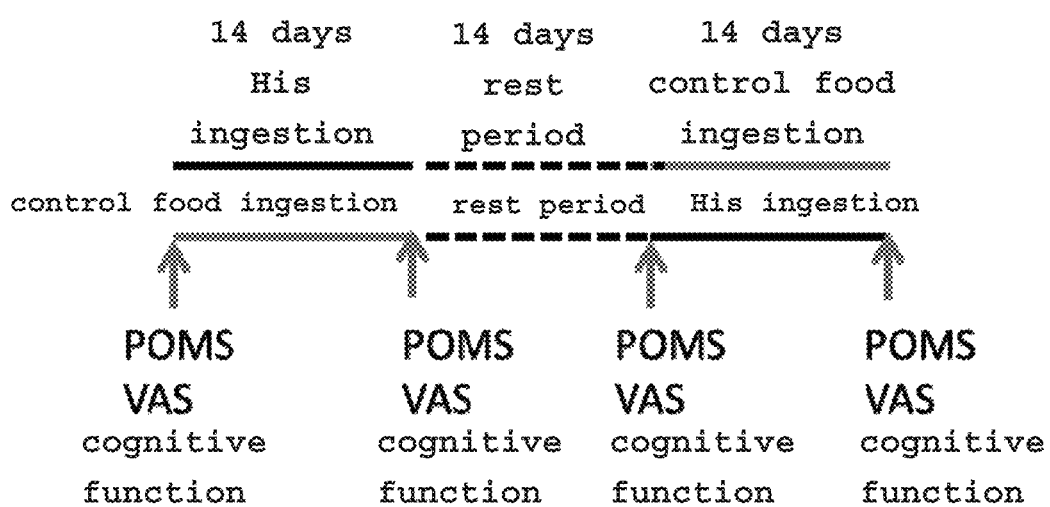
FIG. 4A shows the protocol for verifying changes in the mood, motivation and cognition relating to the mental energy of male feeling degraded quality of sleep and fatigue due to the ingestion of histidine for 14 days.
Figure 4B:
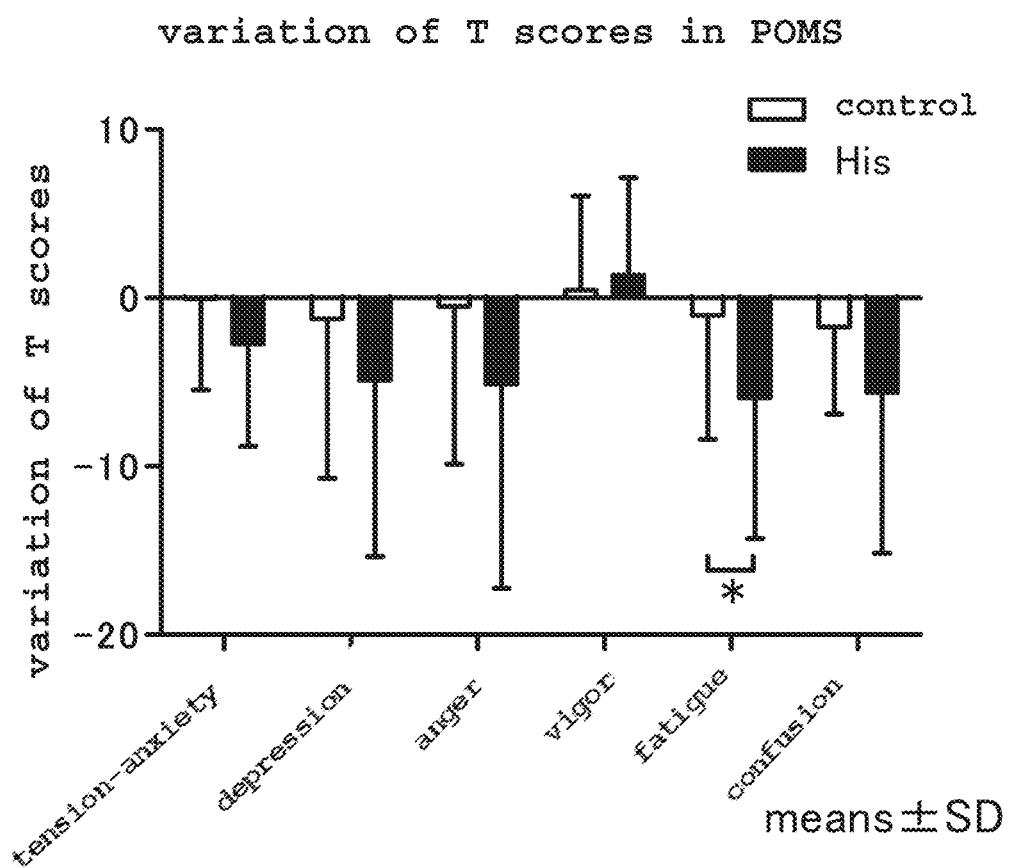
FIG. 4B shows variation of T scores in POMS. *: paired t-test, $p<0.05$.

As shown in the experiment protocol of FIG. 4A, the test subjects ingested capsules containing 1.65 g of L-histidine as a daily ingestion amount (5 capsules (hard capsule #2 WHITE OP B/C) containing 0.33 g of L-histidine alone), or control sample capsules (5 capsules containing equal volume of cellulose) for 14 days. After the completion of 14 day ingestion, a 14 day resting period was taken. After the resting period, they ingested the capsules not ingested before the resting period.

On the initial day and the day after completion of the capsule ingestion period, the test subjects answered POMS and the VAS questionnaires (fatigue, depression, vague sense, drowsiness, clear thinking, motivation, attentiveness, concentration) relating to mental energy, and cognitive function measurement task CogHealth (under higher difficulty conditions by simultaneously including mental arithmetic task as well) to measure recognition. Furthermore, they answered VAS questionnaires after completion of CogHealth. Evaluation after completion of CogHealth reveals the difference of the state between after and before the work-load.

Figure 4D:
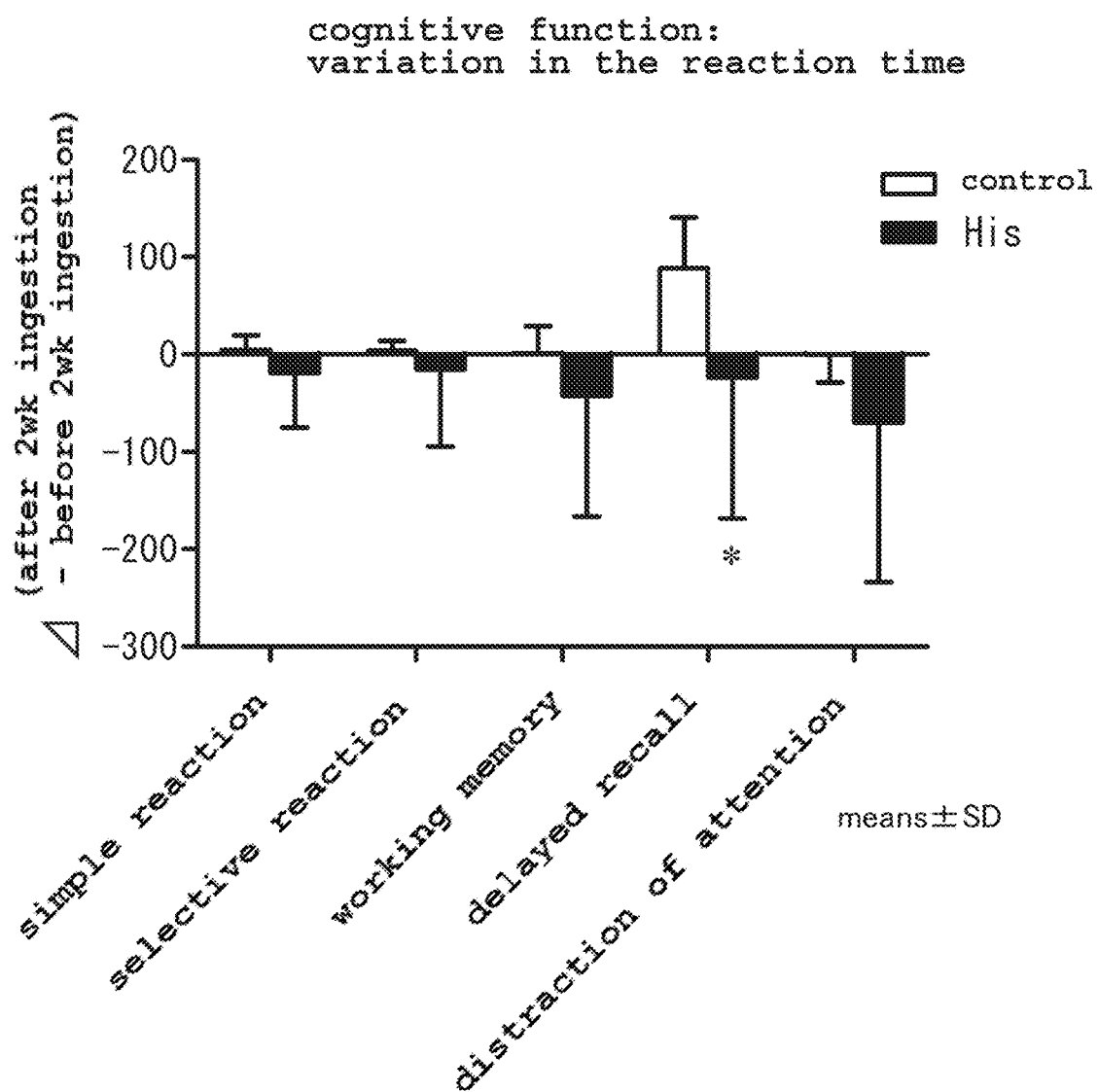
FIG. 4D shows variation in the reaction time in cognitive functioning test. *: paired t-test, $p<0.05$.
Figure 4E:
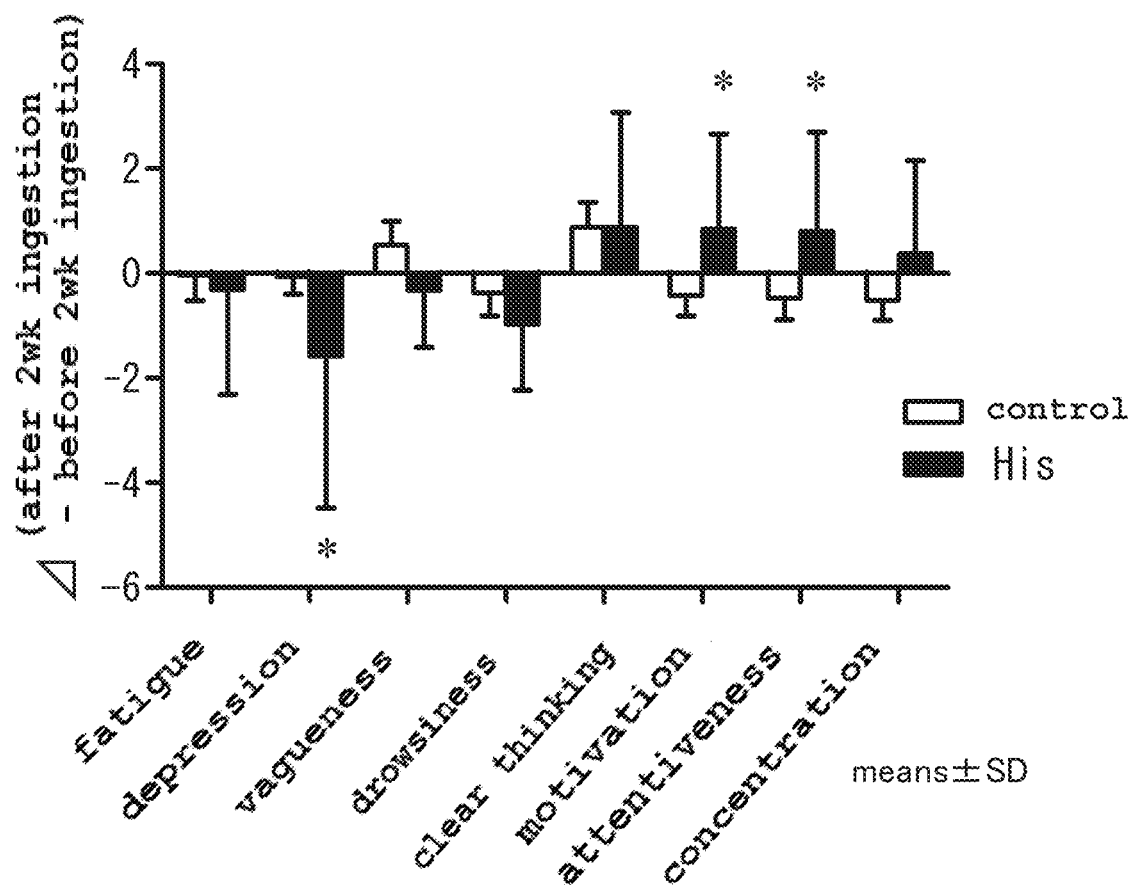
FIG. 4E shows variation of each index in VAS after cognitive functioning test. *: paired t-test, $p<0.05$.

The results are shown in FIGS. 4B to 4E. As compared to the test subjects who ingested the control food, the fatigue factor scores of POMS significantly decreased (paired t-test: $p<0.05$) (FIG. 4B) and the sense of clear thinking, motivation, and attentiveness significantly increased (paired t-test: $p<0.05$) in VAS questionnaires relating to mental energy (FIG. 4C) in the test subjects who ingested histidine for 14 days. In the intellectual work efficiency, ingestion of histidine shortened the reaction time of cognitive function measurement task and significantly decreased the reaction time of delayed recall task (paired t-test: $p<0.05$) as compared to ingestion of the control food (FIG. 4D). In VAS questionnaires after completion of CogHealth, moreover, the sense of depression significantly decreased and the sense of motivation and attentiveness significantly increased (paired t-test: $p<0.05$) (FIG. 4E). This means that an increase in motivation and attentiveness can be maintained, and feeling of depression by burden can be suppressed, even when cognitive work is loaded.

From the above results, it was clarified that an agent containing histidine can improve mental energy, particularly mood, motivation and cognition.

Example 5: Verification of Effect of Single Histidine (His) Ingestion in Males Feeling Decrease in the Quality of Sleep and Fatigue Twenty males of 45 years old to less than 65 years old, who received total evaluation of not less than 17 points in the "self-diagnosis fatigue questionnaire" (Fatigue Science Laboratory Inc.) performed in advance, felt decrease in the quality of sleep (generally PSQI≥6), and obtained fatigue factor T scores of not less than 60 points in POMS, were selected, and randomly divided into 2 groups (10 per group). The effect of single ingestion of histidine and control food (equal volume of cellulose) was compared in each group.

Figure 5A:
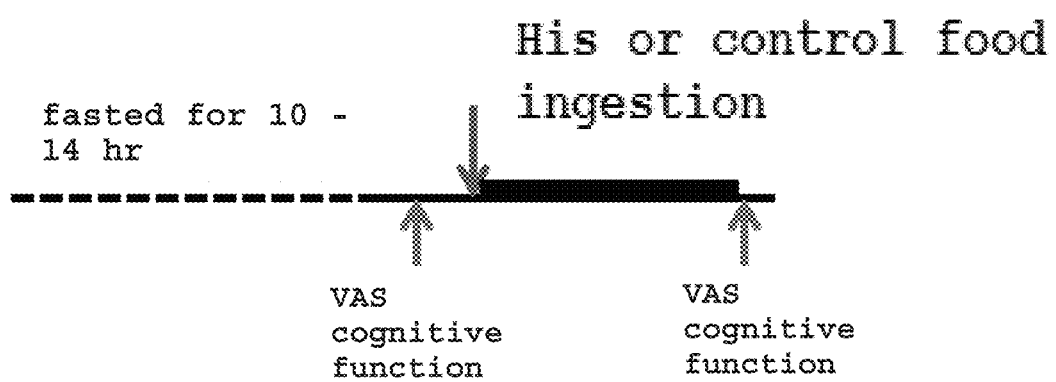
FIG. 5A shows the protocol for verifying changes in the mood, motivation and cognition relating to the mental energy of male feeling a decrease in the quality of sleep and fatigue due to single ingestion of histidine.

As shown in the experiment protocol of FIG. 5A, the test subjects took the same meals for 3 days before the experiment, fasted for 10 to 14 hr, and ingested capsules containing 1.65 g of L-histidine as a single ingestion amount (5 capsules (hard capsule #2 WHITE OP B/C) containing 0.33 g of L-histidine alone), or control sample capsules (5 capsules containing equal volume of cellulose).

Before and 1 hr after ingestion of capsules, the test subjects answered the VAS questionnaires (fatigue, depression, vague sense, drowsiness, clear thinking, motivation, attentiveness, concentration) relating to mental energy, and cognitive function measurement task CogHealth (under conditions with higher difficulty by simultaneously including mental arithmetic task as well) to measure recognition. Furthermore, they answered VAS questionnaires after completion of CogHealth. Evaluation after completion of CogHealth reveals the difference of the state between after and before the work-load.

Figure 5B:
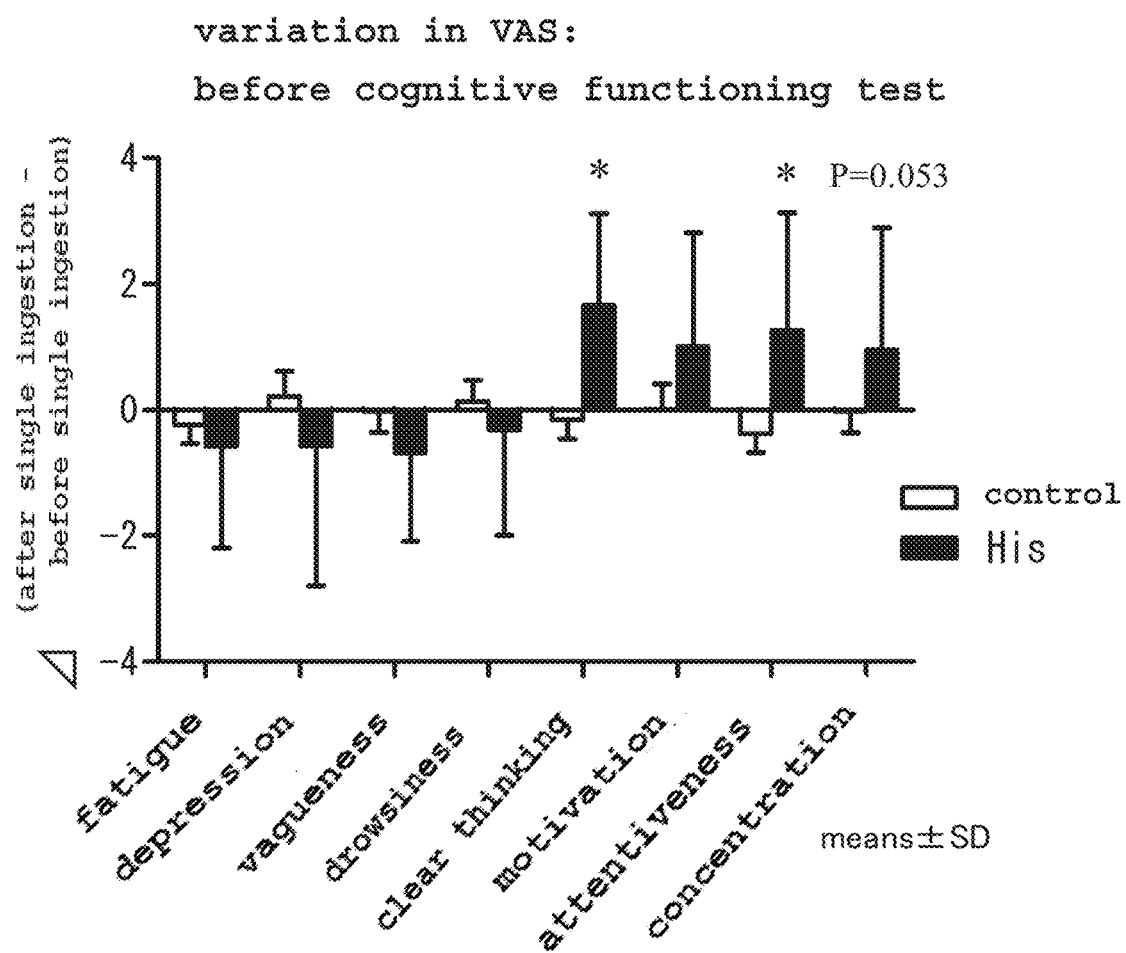
FIG. 5B shows variation of each index in VAS before cognitive functioning test. *: paired t-test, $p<0.05$.

The results are shown in FIGS. 5B and C. It was found that the work time in 5 kinds of brain function measurement indices was shortened in the test subjects who ingested histidine, as compared to the test subjects who ingested the control food, even though the indices relating to cognition did not show a significant change. In VAS questionnaires relating to mental energy, the sense of clear thinking and attentiveness significantly increased (paired t-test: $p<0.05$) and the sense of concentration tended to increase (FIG. 5B). In VAS questionnaires after completion of CogHealth, moreover, the sense of vagueness significantly decreased (paired t-test: $p<0.05$), the sense of depression tended to decrease, and the sense of concentration tended to increase (FIG. 5C). This means that ingestion of histidine may be able to suppress vague sense and the sense of depression due to burden and maintain concentration, even when cognitive work is loaded.

From the above results, it was clarified that an agent containing histidine can improve mental energy, particularly mood.

As mentioned above, continuous ingestion of histidine for 2 weeks showed improvement of mental energy, and a single ingestion of histidine showed improvement of mental energy. Ingestion of histidine did not show problematic variation in general properties, hematology, and blood biochemistry from the aspects of safety.

Example 6: Biorhythm Phase Regulating Action of Histidine (His) Ingestion

A phase regulating action of histidine on a mouse reared under 24 hr dark conditions was evaluated.

When a mouse is reared under 24 hr dark conditions, the mouse starts to act in a cycle specific to the biological clock (also referred to as free run, meaning freed from synchrony), since the outside information (light-dark cycle of light) cannot be obtained. When the free run cycle is converted to 24 hr and indicated as circadian time on the horizontal axis, 12 hours of the former half thereof is called a subjective light period (time zone judged to be daytime by biological clock: CT0-12), and the latter half is called a subjective dark period (time zone judged to be night by biological clock: CT12-24).

Under such conditions, locomotor activity of mice (behavioral pattern in free run cycle) was measured using an emission infrared detector type locomotor activities sensor (Digital acquisition system; NS-AS01, Neuroscience Inc, Tokyo, Japan). Furthermore, a feed added with 45 mg of L-histidine per 1 g of a general feed was prepared, and used to replace the general feed for only 4 hours in one day to allow for ingestion. The time zone for ingestion was CT2-6 (subjective light period) or CT14-18 (subjective dark period). Such replacement of the feed was performed for 4 days, and change of phase of the behavioral pattern was judged.

Figure 6:
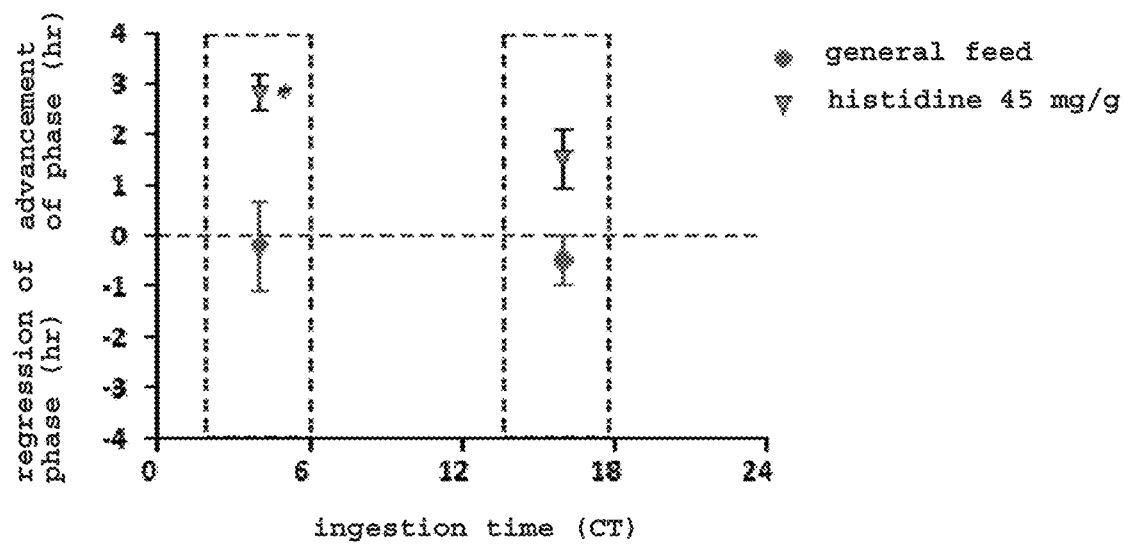
FIG. 6 shows a phase advance effect on biorhythm by the ingestion of histidine. *: unpaired t-test.

The phase shift of the behavior start time of the mice when the date of evaluation criteria was set to 4 days after the final ingestion day of the histidine high content feed is shown in FIG. 6. It was clarified that histidine ingestion in the subjective light period significantly advances the circadian rhythm. In addition, histidine ingestion in the subjective dark period also tended to advance the circadian rhythm.

Figure 7:
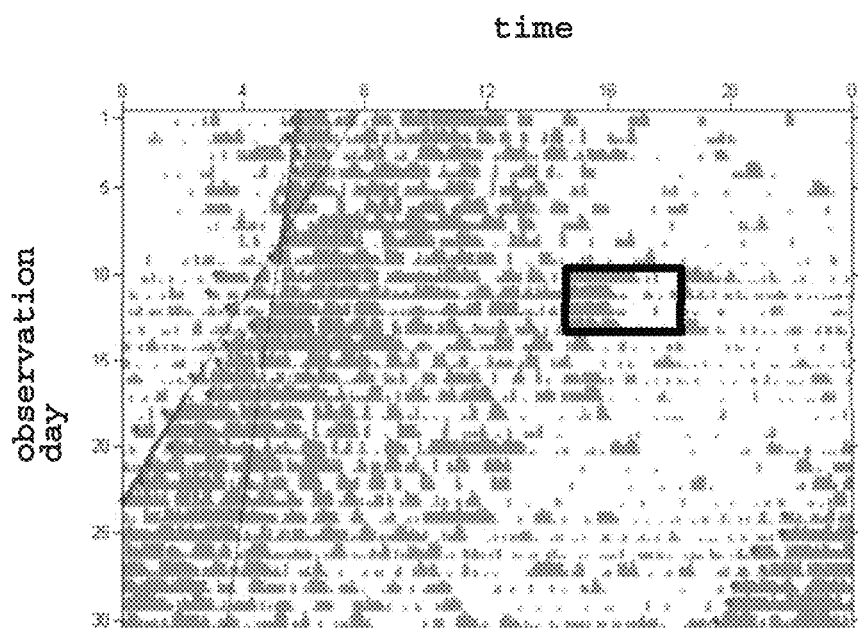
FIG. 7 shows one embodiment in the Examples, which shows that the biorhythm phase can be adjusted by the ingestion of histidine, wherein the horizontal axis shows time, and the vertical axis shows the observation days, and an increase in the locomotor activities for each observation day is shown in a bar graph.

Furthermore, one embodiment of the Example is shown in FIG. 7. In FIG. 7, the horizontal axis shows time, the vertical axis shows observation days, and an increase in the locomotor activities for each observation day is shown in a bar graph. The ingestion of histidine in CT2-6 (time zone enclosed in black square in FIG. 7) shortened the cycle of activity rhythm, and the mean under the same conditions was shortened by $0.34\pm0.08$ hr (n=4). In human, the rhythm created by the inner body clock is generally considered to be a little longer than 24 hr, and since many of the abnormalities of biorhythm are caused by regression of circadian rhythm, the biorhythm can be normalized (closer to 24 hr cycle in human) by advancing the circadian rhythm or shortening the cycle by ingestion of histidine at a suitable time.

From the above results, it was confirmed that an agent containing histidine is effective as a diurnal rhythm normalizing agent, a biorhythm improving agent, a circadian rhythm sleep disorder improving agent, a delayed sleep phase syndrome improving agent, a therapeutic agent for jet lag, a prophylactic agent for jet lag, or an agent for improving ill health associated with working in shifts.

Example 7: Improvement of Asynchrony of Biorhythm with the Outside World by Histidine (His) Ingestion Aged mice of 22 to 24 months of age being reared under generally light and dark environment were divided into two groups, and the effect of the ingestion of histidine drinking solution was studied. The histidine ingestion period was set to 9 days, during which period aqueous L-histidine solution (corresponding to L-histidine 1.2 w/v %) was given for ingestion by mounting a water inlet on a 50 mL centrifuge tube, whereby about 1.2 g/kg body weight of histidine was ingested per day. In the histidine ingestion group of aged mice, samples were taken from the auricle by changing the position over time on 8 to 9 days from the start of the ingestion of the aqueous histidine solution, and 5 kinds of clock genes (Bmal1, Dbp, Per1, Per2, Reverb-alpha) of the peripheral tissue were analyzed as an index of biorhythm. In the simultaneous stage, the clock genes of the auricle of the aged mice and young mice (4 months old) that ingested tap water were analyzed as comparison targets. It is known that the clock genes are sufficiently synchronized with the environment of the outside world, and clear amplitudes and phase pattern are obtained in young, generally-reared mice. On the other hand, it has been reported that, when light cycle is artificially changed, the expression of clock gene also changes in response thereto, in addition to the behavioral pattern (reference document: The Journal of Clinical Investigation 2010 July; 120(7):2600-9, which is incorporated herein by reference in its entirety).

To be specific, gene expression of the clock gene was quantified at each time point, and the amplitudes and phase of the oscillation of expression of the clock gene of each individual were determined by approximation on the cosine curve. The average amplitude and phase of the oscillation of expression of 5 clock genes of each individual were compared to those of young mice and converted into numerical values.

Figure 8:
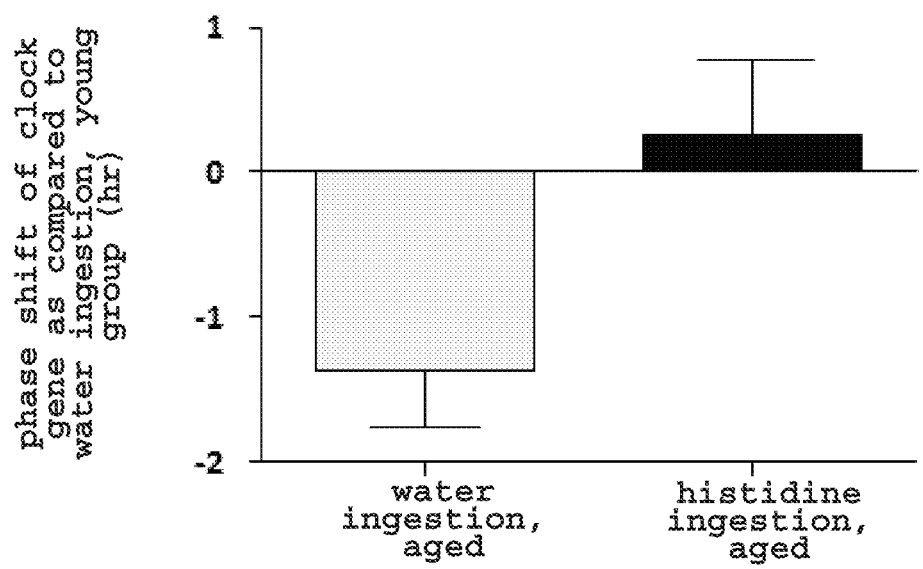
FIG. 8 shows change of phase in the oscillation of expression of clock gene due to the ingestion of histidine.

The results are shown in FIG. 8. When tap water was ingested, comparison of aged mice and young mice revealed that the amplitude of oscillation of the expression of clock gene decreased in aged mice. Moreover, phase shift of the oscillation of expression of the clock gene, which is considered to have been caused by a decrease in the amplitude, occurred in general aged mice, and the phase advanced by about one hour. In contrast, histidine ingestion suppressed phase advancement even in aged mice, and the average of measured 5 clock genes reached the same level as in young mice (FIG. 8). In an experiment using young mice, it has been clarified that when a feed having a histidine content lowered to 20% of that of general feeds is given for 1 to 2 weeks, the locomotor activities at the active phase start time decrease by about 63% and the peak of activity is shifted backward, from which histidine ingestion is assumed to be effective for asynchrony of biorhythm with the outside world even at a young age.

From the above results, it was shown that an agent containing histidine is effective as an agent having an action to improve various symptoms due to asynchrdny of biorhythm with the outside world, for example, one or more indices selected from the group consisting of jet lag-like symptoms including early wakening, headache, tinnitus, palpitation, nausea, abdominal pain and diarrhea, fatigue-like symptoms including a decrease in clear thinking, motivation, attentiveness and concentration, depression, and drowsiness.

Formulation Example 8: Histidine-Containing Tablet

A histidine-containing tablet having the following combination is produced by tableting according to a conventional method. The tablet weight is 340 mg.

TABLE 1

| each component | combination ratio (%) |
|---|---|
| L-histidine | 76.048 |
| starch syrup of reduced malt sugar | 12.446 |
| cellulose | 9.506 |
| calcium stearate | 2 |
| total | 100 |

INDUSTRIAL APPLICABILITY

The food etc. of the present invention can effectively improve the mental energy and improve biorhythm, and is superior in safety since the active ingredient thereof is amino acid. Therefore, the food etc. of the present invention can be utilized not only in the food field but also in the medicament field.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings.

It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of improving mental energy, which comprises administering not less than 0.3 g of histidine as an ingestion amount per meal to a human subject in need thereof, wherein said subject exhibits a Pittsburgh Sleep Quality Index (PSQI) of not less than 6 and/or a factor T score of not less than 60 points in Profile of Mood Sates (POMS), wherein said histidine is administered in a liquid composition which comprises histidine in an amount not less than 3 w/v % wherein said subject is a human of 45 years old to less than 65 years old.

2. A method of improving biorhythm, which comprises administering not less than 0.3 g of histidine as an ingestion amount per meal to a human subject in need thereof, wherein said subject exhibits a Pittsburgh Sleep Quality Index (PSQI) of not less than 6 and/or a factor T score of not less than 60 points in Profile of Mood Sates (POMS), wherein said histidine is administered in a liquid composition which comprises histidine in an amount not less than 3 w/v % wherein said subject is a human of 45 years old to less than 65 years old.

3. A method according to claim 1, which comprises administering an amino acid other than histidine or a substance convertible to an amino acid other than histidine by hydrolysis in an amount of not more than 8 g per meal based on amino acid other than histidine.

4. A method according to claim 1, further comprising administering at least one kind of additive selected from the group consisting of an excipient, a corrigent, and a flavor.

5. A method according to claim 4, wherein said corrigent is citric acid.

6. A method according to claim 1, wherein said histidine is administered in the form of a food.

7. A method according to claim 1, wherein said histidine is administered in the form of a drink.

8. A method according to claim 1, which comprises administering not less than 0.7 g of histidine as an ingestion amount per meal to said subject in need thereof.

9. A method according to claim 2, which comprises administering an amino acid other than histidine or a substance convertible to an amino acid other than histidine by hydrolysis in an amount of not more than 8 g per meal based on amino acid other than histidine.

10. A method according to claim 2, further comprising administering at least one kind of additive selected from the group consisting of an excipient, a corrigent, and a flavor.

11. A method according to claim 10, wherein said corrigent is citric acid.

12. A method according to claim 2, wherein said histidine is administered in the form of a food.

13. A method according to claim 2, wherein said histidine is administered in the form of a drink.

14. A method according to claim 2, which comprises administering not less than 0.7 g of histidine as an ingestion amount per meal to said subject in need thereof.

15. A method according to claim 1, wherein said liquid composition comprises histidine in an amount not less than 5 w/v %.

16. A method according to claim 2, wherein said liquid composition comprises histidine in an amount not less than 5 w/v %.

17. A method of improving mental energy, which comprises administering not less than 0.3 g of histidine as an ingestion amount per meal to a human subject in need thereof, wherein said subject exhibits a Pittsburgh Sleep Quality Index (PSQI) of not less than 6 and/or a factor T score of not less than 60 points in Profile of Mood Sates (POMS), wherein said histidine is administered in an amount of not less than 1.6 grams per day and wherein said subject is a human of 45 years old to less than 65 years old.

18. A method according to claim 17, which comprises administering an amino acid other than histidine or a substance convertible to an amino acid other than histidine by hydrolysis in an amount of not more than 8 g per meal based on amino acid other than histidine.

19. A method according to claim 17, further comprising administering at least one kind of additive selected from the group consisting of an excipient, a corrigent, and a flavor.

20. A method according to claim 19, wherein said corrigent is citric acid.

21. A method according to claim 17, wherein said histidine is administered in the form of a food.

22. A method according to claim 17, wherein said histidine is administered in the form of a drink.

23. A method of improving biorhythm, which comprises administering not less than 0.3 g of histidine as an ingestion amount per meal to a human subject in need thereof, wherein said subject exhibits a Pittsburgh Sleep Quality Index (PSQI) of not less than 6 and/or a factor T score of not less than 60 points in Profile of Mood Sates (POMS), wherein said histidine is administered in an amount of not less than 1.6 grams per day and wherein said subject is a human of 45 years old to less than 65 years old.

24. A method according to claim 23, which comprises administering an amino acid other than histidine or a substance convertible to an amino acid other than histidine by hydrolysis in an amount of not more than 8 g per meal based on amino acid other than histidine.

25. A method according to claim 23, further comprising administering at least one kind of additive selected from the group consisting of an excipient, a corrigent, and a flavor.

26. A method according to claim 25, wherein said corrigent is citric acid.

27. A method according to claim 23, wherein said histidine is administered in the form of a food.

28. A method according to claim 23, wherein said histidine is administered in the form of a drink.

* * * * *